(12) United States Patent
Michl et al.

(10) Patent No.: US 6,628,016 B2
(45) Date of Patent: Sep. 30, 2003

(54) MOLECULAR DIPOLAR ROTORS

(75) Inventors: Josef Michl, Boulder, CO (US); John C. Price, Longmont, CO (US); Thomas F. Magnera, Louisville, CO (US)

(73) Assignee: California Molecular Electronics Corporation, San Jose, CA (US)

( * ) Notice: Subject to any disclaimer, the term of this patent is extended or adjusted under 35 U.S.C. 154(b) by 80 days.

(21) Appl. No.: 09/812,647

(22) Filed: Mar. 20, 2001

(65) Prior Publication Data

US 2001/0033937 A1 Oct. 25, 2001

Related U.S. Application Data

(60) Provisional application No. 60/190,648, filed on Mar. 20, 2000.

(51) Int. Cl.[7] .................... K02K 44/00; C01B 33/08; C07F 7/04; C07F 7/10

(52) U.S. Cl. .................. 310/10; 423/342; 556/415; 556/28

(58) Field of Search .......................................... 310/10

(56) References Cited

U.S. PATENT DOCUMENTS

| | | | | |
|---|---|---|---|---|
| 5,204,573 A | * | 4/1993 | Bederson et al. | 310/198 |
| 5,405,550 A | | 4/1995 | Michl et al. | 252/299 |
| 5,876,830 A | | 3/1999 | Michl et al. | 428/114 |
| 6,333,147 B1 | * | 12/2001 | Toya | 430/619 |
| 6,342,343 B1 | * | 1/2002 | Toya | 430/619 |
| 6,350,569 B1 | * | 2/2002 | Watanabe et al. | 430/619 |
| 6,376,166 B1 | * | 4/2002 | Oya et al. | 430/619 |
| 2002/0068295 A1 | * | 6/2002 | Madou et al. | 435/6 |
| 2002/0068304 A1 | * | 6/2002 | Urry | 435/7.1 |

OTHER PUBLICATIONS

Asturnian, R.D. (1997) "Thermodynamics and Kinetics of a Brownian Motor" Science 276:917–922.
Balzani, V. et al. (1998) "Molecular Machines" Acc Chem. Res. 31:405–414.
Baranova, N.B., and Zel'dovich, B. (1978) "Separation of Mirror Isomeric molecules by Radio–Frequency Electric Field of Rotating Polarization" Chem. Phys. Lett. 57(3):435–437.
Barbara, P.F. et al., "Contemporary Issues in Electron Transfer Research", (1996) J. Phys. Chem. 100:13148–13168.
Bedard, T.C., and Moore, J.S. (1995) "Design and Synthesis of a 'Molecular Turnstile'" J. Am. Chem. Soc. 117:10662–10671.
Bermudez, V. et al., (Aug. 2000) "Influencing Intramolecular Motion with an Alternating Electric Field" Nature 406:608–611.
Clayden, J.and Pink, J.H. (1998) "Concerted Rotation in a Tertiary Aromatic Amide: Towards a simple Molecular Gear" Angew. Chem. Internat. Ed. Engl. 37:1937–1939.
Dalberth, M.J. et al. (1998) "Improved Low Frequency and Microwave Dielectric Response in Strontium Titanate Thin Films Grown by Pulsed Laser Ablation" Applied Physics Letters 72(4):507–509.

(List continued on next page.)

Primary Examiner—Nestor Ramirez
Assistant Examiner—Pedro J. Cuevas
(74) Attorney, Agent, or Firm—Greenlee, Winner & Sullivan, P.C.

(57) ABSTRACT

Molecular dipolar rotors comprising a base, an axle connected to said base and oriented substantially perpendicular to said base, and a rotor portion having an electric dipole moment are provided. The molecular dipolar rotors may be attached to a surface. Arrays of molecular dipolar rotors attached to surfaces are provided. Molecular dipolar rotors are useful in preparation of small devices.

20 Claims, 11 Drawing Sheets

OTHER PUBLICATIONS

Davis, W.B. et al., "Electron Transfer Rates in Bridged Molecular Systems: A Phenomenological Approach to Relaxation" (1997) J. Phys. Chem. A. 101:6158–6164.

DeLeeuw, S. W. et al., "Molecular Dipole Chains: Excitations and Dissipation" J. Phys. Chem. B (1998) 102:3876–3885.

Elschenbroich, C. and Salzer, A., Organometallics A Concise Introduction, 2nd Edition, (1992) Chapters 13–16, VCH Publishers: Weinheim, Germany.

Feynman, R.P., In Miniaturization, Gilbert, H.D., Ed.; Reinhold: New York (1961) Chapter 16 "There's Plenty of Room at the Bottom" p. 282–296.

Fredj, E. et al., "Semiclassical molecular dynamics simulations of low–temperature clusters: Applications to $(Ar)_{13}$; $(Ne)_{13}$; $(H_2O)_n$, n=2,3,5" (1996) J. Chem. Phys. 105:1121–1130.

Garrett, M.F. et al., (1964) "The Thermal Isomerization of C–Phenyldicarbaundecaborate (12)" J. Am. Chem. Soc. 86:5016–5017.

Gimzewski, J., (1998) "Molecules, nanophysics and nanoelectronics", Phys. World 11:29–33.

Gimzewski, J.K. et al. (1998) "Rotation of a Single Molecule Within a Supramolecular Bearing" Science 281:531–533.

Grimes, R.N., (1992) "Boron–Carbon Ring Ligands in Organometallic Synthesis" Chem Rev. 92:251–268.

Grimes, R.N., (1996) "Metal–Carborane Multidecker Sandwich complexes as Building Blocks for New Materials" Appl. Organomet. Chem. 10:209–225.

Harrison, R.M. et al. "Towards a Square Grid Polymer: Synthesis and Structure of Pedestal–Mounted Tetragonal Star Connectors, $C_4R_4$–Co–$C_5Y_5$" (1997) Organometallics 16:3401–3412.

Harrison, R.M., et al. "Towards Designer Solids" in Modular Chemistry, (1997) Michl, J., ed., Kluwer, Dordrecht, The Netherlands, pp 1–16.

Hoffman, B.M. and Ratner, M.A. "Reorganization energies and rate constants for electron reactions in glass–forming media and proteins" (1996) Inorg. Chim. Acta 243:233–238.

Jortner, J. and Ratner, M., Molecular Electronics: A 'Chemistry for the $21^{st}$ Century' monograph, (1997) Blackwell: London, England.

Kelly, T.R. et al., (1997) "In Search of Molecular Ratchets" Angew. Chem. Internat. Ed. Engl. 36:1866–1868.

Kemp, M. et al. "Molecular Wires: Extended Coupling and Disorder Effects" (1996), J. Phys. Chem. 100:8349–8355.

Kemp, M. et al., "Molecular Wires: Resonances, Staircases, Rectification, Bonding and Speculation", in Atomic and Molecular Wires, (1997) Roth, S., Joachim, C., Ed., Kluwer Academic Publishers, Dordrecht: The Netherlands, pp. 203–217.

King, B.T., Ph.D. Dissertation, University of Colorado, Boulder (2000, published in Dissertation Abstracts Jun. 2001).

Kosloff, R. et al. "Dynamics and Relaxation in Interacting Systems: Semigroup Methods" (1997) 106:7036–7043.

Koumura, N. et al. (Sep. 1999) "Light–driven Monodirectional Molecular Rotor" Nature 401:152–155.

Kudinov, A.R. et al. (Jan. 1999) "π–Complexes of Monoanionic Carborane Ligand $[9–(Me_2S)–7,8–C_2B_9H_{10}]$ with $[\eta–C_5R_5Fe]^+$ (R=H, Me) and $[\eta–C_4Me_4Co]^+$ Cationic Fragments" Russian Chem. Bull. 48:176–178.

Madura, J.D. et al. In Encyclopedia of Computational Chemistry, Wiley: Chichester, England (1998) vol. 1, p. 141–154.

Magnera, T.F. and Michl, J. "Towards a more regular square grid polymer", Atualidades de Fisico–Quimica Organica (1998) 50–55.

Magnera, T.F. et al., "Synthesis and Handling of Single Sheets of a Covalent Monolayer Square Grid Polymer" in Nanostructural materials: Clusters, Composites, and Thin Films,(1997) Moskovits, M., Shalaev, V., Eds., ACS Symposium Series 679, American Chemical Society: Washington, D.C. pp. 213–220.

Magnera, T.F. et al., "Synthesis of a covalent Square Grid", In Science and Technology of Polymers & Advanced Materials, Ed. Prasad, P.N. (1998) Plenum: New York, pp. 385–391.

Magnera, T. F. et al., "Organometallic 'Molecular Tinkertoy' Approach to Planar Grid Polymers" (1997) J. Organomet. Chem. 548:83–89.

Michl, J., "Staffanes", (1995) McGraw Hill Yearbook of Science and Technology, McGraw Hill, New York, pp. 391–395.

Michl, J. "Supramolecular Assemblies from "Tinkertoy" Rigid–Rod Molecules" in *Mesomolecules: From Molecules To Materials*, (1995) Mendenhall, D., Greenberg, A., and Liebman, J. Eds: Chapman & Hall, New York: pp. 132–160.

Mislow, K., (1989) "Molecular Machinery in Organic Chemistry" Chemtracts—Organic Chemistry 2:151–174.

Mujica, V. et al., "Current–voltage characteristics of molecular wires: Eigenvalue staircase, coulomb blockade, rectification" (1996) J. Chem. Phys. 104:7296–7305.

Mujica, V. et al., "Electron conduction in molecular wires. II. Application to scanning tunneling microscopy", (1994) J. Chem. Phys. 101:6856–6864.

Mujica, V. et al., "Electron Conduction in molecular wires. I. A scattering formalism" (1994) J.Chem. Phys. 101:6849–6855.

Noji, H. et al., (1997) "Direct observation of the rotation of $F_1$–ATPase" Nature 386:299–302.

Norris, L.S. et al., "Møller–Plesset perturbatin theory applied to vibrational problems" (1996), J.Chem. Phys. 105:11261–11267.

Patashinski, A.Z. and Ratner, M.A. "Inherent amorphous structures and statistical mechanics of melting", (1997) J. Chem. Phys. 106:7249–7256.

Pospíšil, L. et al., "Towards a Hexagonal Grid Polymer: Interaction of Tentacled 1,3,5–Tricarboranylbenzene Derivatives with Mercury Surface" (1997) Langmuir 13:6294–6301.

Radziszewski, J. G. et al., "Polarized IR Spectra of Photooriented Matrix–Isolated Free–Base Porphyrin Isotopomers", (1995) J.Phys. Chem., 99:14254–14260.

Roitberg, A. et al, "Anharmonic Wave Functions of Proteins: Quantum Self Consistent Field Calculations of BPTI", (1995), Science, 268:1319–1322.

Roitberg, A.E. et al., "A Vibrational Eigenfunction of a Protein: Anharmonic Coupled–Mode Ground and Fundamental Excited State of BPTI", (1997) J. Phys Chem. B 101:1700–1706.

Sauvage, J.P., "Transition Metal –Containing Rotaxanes and Catenanes in Motion Machines and Motors" (1998) Acc Chem. Res.31:611–619.

Saxena, A.K. and Hosmane, N.S., (1993) "Recent Advances in the Chemistry of Carborane Metal Complexes Incorporating d- and f-Block Elements" Chem. Rev. 93:1081–1124.

Schoberl, U. et al., "Towards a Hexagonal Grid Polymer: Synthesis, Coupling, and Chemically Reversible Surface-Pinning of the Star Connectors, 1,3,5-$C_6H_3(CB_mH_{10}CX)_3$" (1997) J. Am. Chem. Soc., 119:3907–3917.

Sim, E. et al. (1999) "Molecular Dipole Chains II" J.Phys. Chem. B, 103:8663–8670.

Sohlberg K. et al., (1997) Application of Rigid–Body Dynamics and Semiclassical.

Mechanics to Molecular Bearings Nanotechnology 8:103–111.

Space, B. et al., (1996) "Feasability of Using Photophoresis to Create a concentration Gradient of Solvated Molecules" J. Chem. Phys. 105:9515–9524.

Vacek, J and Michl, J. "A Molecular 'Tinkertoy' Construction Kit: Computer Simulation of Molecular Propellers" (1997) New J. Chem. 21:1259–1268.

Vacek, J. and Michl, J. "Molecular Dynamics of a Grid-Mounted Molecular Dipolar Rotor in a Rotating Electric Field" (May 2001) Proc. Natl. Acad. Sci. 98:5481–5486.

Vekhter, B.G. and Ratner, M.A., "Energy and charge trapping by localized vibrations: Electron–vibrational coupling in anharmonic lattices", (1995) Phys. Rev. B. 51:3469–3475.

Vekhter, B.G. and Ratner, M.A., "Electron Transfer in Mixed–Valence Clusters: Spin–Dependent Dielectric Loss and Hamiltonian Parameters", (1995) J. Phys. Chem. 99:2656–2661.

Vendik, O.G., "Dielectric Nonlinearity of the Displacive Ferroelectrics at UHF" (1976) Ferroelectrics 12:85–90.

Wegner, P.A. and Hawthorne, M.F., (1966) "Preparation and Properties of [$\pi$-($C_6H_5$)$_4C_4$]Pd[$\pi$-$B_9C_2H_{11}$]", Chem. Comm. 861–862.

Wiesboeck, R.A. and Hawthorne, (1964) "Dicarbaundecaborane(13) and derivatives", J. Am. Chem. Soc. 86:1642–1643.

Zharov, I., Ph.D. Dissertation, Univ. of Colorado, Boulder (2000 published in Dissertation abstracts Jan. 2001).

Zorski, H. and Infeld, E. (1992) "New soliton equation for dipole chains", Phys. Rev. Lett. 68:1180–1183.

Jean–Pierre Sauvage, Transition Metal–Containing Rotaxanes and Catenanes in Motion: Toward Molecular Machines and Motors, American Chemical Society's Accounts Of Chemical Research / vol. 31, No. 10, 1998, pp 611–619.*

Alan Hall, Molecular Model–T, American Scientific, Sep. 21, 1999.*

Balzani et al., Constructing Molecular Machinery: A Chemically–Switchable [2] Catenane, Journal of American Chemical Societ 2000, 122, 3542–3543.*

Jianwei J. Li and Weihong Tan, A single DNA Molecule Nanomotor, Nano Letters, 2002, vol. 2, No. 4, 315–318.*

Marina Alexandra Lyshevski, Motion of Brownian Molecular Motor: Nanoscale–Based Modeling, Analysis, and Control, Proceedings of the American Control Conference, Arlington, VA, Jun. 25–27, 2001.*

T.Ross Kelly, Progress toward a Rationally Designed Molecular Motor, American Chemical Society's Accounts Of Chemical Research / vol. 34, No. 6, 2001, pp 514–522.*

Ben L. Fringa, In Control of Motion: From Molecular Switches to Molecular Motors, American Chemical Society's Accounts Of Chemical Research / vol. 34, No. 6, 2001, pp 504–513.*

Amendola et al., Molecular Machines Based on Metal Ion Translocation, American Chemical Society's Accounts Of Chemical Research / vol. 34, No. 6, 200, pp 488–493.*

Schalley et al., On the Way to Rotaxane–Based Molecular Motors: Studies in Molecular Mobility and Topological Chirality, American Chemical Society's Accounts Of Chemical Research / vol. 34, No. 6, 2001, pp 465–476.*

Akira Hadara, Cyclodextrin–Based Molecular Machines, American Chemical Society's Accounts Of Chemical Research / vol. 3, No. 6, 2001, pp 456–464.*

Ballardini et al., Artificial Molecular–Level Machines: Which Energy To Make Them Work?, American Chemical Society's Accounts Of Chemical Research / vol. 34, No. 6, 2001, pp 445–455.*

Bustamante et al., The Physics of Molecular Motors, American Chemical Society's Accounts Of Chemical Research / vol. 34, No. 6, 2001, pp 412–420.*

Gary Stix, Waiting for Breackthroughs, American Scientific, Apr. 1, 2001.*

* cited by examiner

MOLECULAR DIPOLAR ROTORS

CROSS-REFERENCE TO RELATED APPLICATIONS

This application takes priority to U.S. provisional patent application Ser. No. 60/190,648, filed Mar. 20, 2000 which is hereby incorporated by reference to the extent not inconsistent with the disclosure herein.

STATEMENT REGARDING FEDERALLY SPONSORED RESEARCH OR DEVELOPMENT

This application was funded, at least in part, by National Science Foundation grant CUE9871917. The federal government may have certain rights in the invention.

This invention is in the general field of nanotechnology and more specifically relates to methods and materials for construction of molecular-scale structures, and devices using the same.

BACKGROUND OF THE INVENTION

Functional nanostructures that allow investigation into fundamental issues in micromechanics, molecular electronics, statistical physics and the materials science of polar dielectrics are needed. In addition, there is a need in the art for a molecular dipolar rotor which will rotate under application of a force for use in functional devices.

BRIEF SUMMARY OF THE INVENTION

Provided are molecular dipolar rotors comprising: a base; an axle which is attached to the base; and a rotor portion with a dipole moment which is attached to the axle. Preferably, the axle is oriented substantially perpendicularly to the surface. The axle may contain a bearing, which may be a bond, such as a metal-to-$\pi$-face bond. Also provided are surface-mounted molecular dipolar rotors (SMDRs) where the base is attached to a surface and arrays of molecular dipolar rotors attached to a surface.

As used herein, "base" means a structure that is capable of attaching to an axle on one side and to a surface on the other side. Bases may comprise a variety of structures. Bases may include one or more aromatic or nonaromatic rings, for example four, five or six membered ring structures; single atoms such as Si or C; and other structures as known in the art. Preferably, the base is wide to provide resistance to rotational axis tilt (pendulum-type motion). The base is capable of being attached to a surface, through functional groups, preferably spontaneously and covalently. Bases include a variety of structures that perform desired functions, and typically carry atoms that act as leaving groups upon attachment of the base with a surface, such as Cl atoms attached to a Si atom. These functional groups can be attached directly to a base or can be attached through tentacles. Tentacles may be alkyl groups where one or more carbons are optionally substituted with one or more members of the group consisting of: metals; O; S; Si; O—R (where R is an alkyl group); —Si (OR)$_3$ (where R is an alkyl group); —HgSCOCH$_3$; —HgSCOR (where R is an alkyl group); halogens, ring structures and other structures. Alkyl groups may be short (1 to 5 carbons), medium (5 to 15 carbons) or long (15–25 carbons). The tentacles provide mechanical inertia against tugging by an outside electric field. This can be provided for with massive atoms, for example Hg atoms included in the tentacles. All tentacles on a base do not have to be the same. Preferably the base allows for attachment of more than one tentacle to a surface, however, in some applications, one tentacle attachment to the base or no tentacle attachment to the base through functional groups (i.e., the base is directly attached to the surface) may be desired. Some tentacles may not be used to attach the base to the surface. Some preferred base and tentacle structures are described herein. The particular functional groups used are dependent on a variety of factors, such as the surface the dipolar rotor is bonded to, as known in the art.

Axles may also comprise a variety of structures. For example, an axle may be a triple bond, a single bond, a metal atom such as a transition metal, or may be more complicated, as in Formula 10 where two metal atoms surround a ring. Other axle structures may be used as desired to connect the base to the rotor. The axle should be rigid enough to prevent undesired motions that interfere with the desired operation.

For many purposes it is best if there is a low (less than about 1 kcal/mol) barrier to rotation about the bearing. The barrier to rotation may be higher, as long as the temperature of the system allows the rotor to overcome the barrier. Preferably there are sites on the rotor portion available for substitution, for mechanical balancing. The rotor portion and axle length are preferably a size that prevents the blades from touching the substrate, unless high friction is desired in a particular application. Preferably the rotor portion is about 0.2 to about 5 nm in diameter, depending on the other parameters chosen. A larger rotor portion will maximize the size of the rotating dipole.

The rotor portion is a part of the dipolar rotor that has a dipole moment. It is preferred that the rotor portion have a large dipole moment. A large electric dipole moment is defined as greater than about 5 D, and is preferably greater than 10 D and can be greater than about 20 D. Dipole moments of 1 D or greater are of interest for a variety of applications. The dipole moment of the rotor portion should be sufficient to cause rotation of the rotor portion in an alternating electric field or upon application of another suitable stimulus. It is preferred that the dipole moment be in the plane of the rotor portion. It is preferred that there is a low barrier to rotation of the rotor portion about the axle. This barrier to rotation is preferably less than 1 kcal/mol, but may be higher if sufficient temperature is applied to the rotor. The rotor portion may comprise a ring structure, preferably an aromatic ring, with opposing "wing tips." Preferably the substituents on the wing tips of the rotor portion carry opposite charges, to provide a large dipole. The rotor portion should be electroneutral overall with large charges preferably located as far as possible from the rotor axis. Preferably the rotor portion is mechanically balanced, with its rotational axis approximately coincident with one of the axes of inertia. The substituents on the wing tips may be polar or charged to provide the rotor portion with a dipole moment. Other rotor portions with a dipole moment may be used, as desired. The rotor may be as simple as mono-, or di-chloromethyl group. Useful substituents are known in the art, such as SO$_3^-$, N$^+$Me$_3$, and others.

The length of the axle may be chosen as desired. Preferably the axle is long enough to prevent the blades of the rotor portion of the dipolar rotor from contacting the surface while rotating.

General structures of dipolar rotors are those shown below:

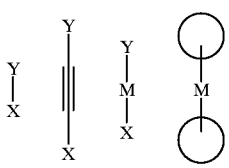

where X is the base, the single bond, triple bond or metal (M) such as a transition metal form the axle and Y is the rotor. The circle represents a ring structure, for example, a four or five or six membered aromatic or nonaromatic ring with suitable substituents as shown and described herein, or various combinations of structures that perform the desired function.

Examples of small dipolar rotors are shown below:

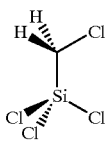

1

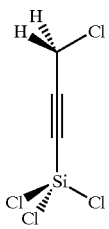

1A

In 1 and 1A, three chlorine atoms are shown attached to silicon. When these structures are bonded to a surface such as glass, the chlorines react with hydroxyl groups on surface and Si—O bonds are formed, and the chlorines are leaving groups. In 1, Si is the base, the Si—C bond is the axle, and H₂Cl is the rotor portion. In 1A, the acetylene bond is the axle. Another small dipolar rotors is shown below.

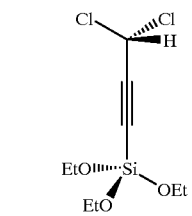

2

The chlorines may be replaced with any halogen. Again, when the rotors shown above are attached to the surface, the ethyl groups may act as leaving groups. The chemistry of attaching molecules to surfaces is well known.

A larger dipolar rotor is shown below.

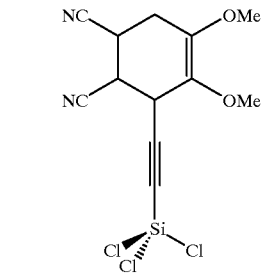

3

In the structure shown above, the ring structure is the rotor portion.

The dipolar rotor may be constructed with various substituents. For example, the substituents on the aromatic ring in structure 3 may be changed. One example of changing substituents in 3 above would be to use substituents that contain positive or negative charges. These structures and substituents are known in the art.

Other more complicated structures are possible, as shown below:

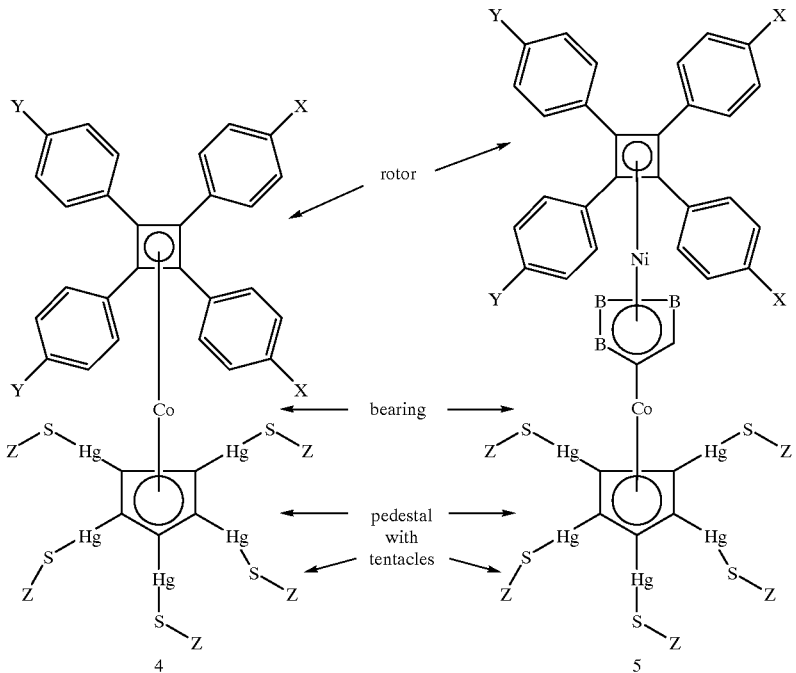

Even larger structures are possible, including those shown below:

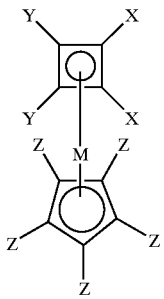

where M is a metal, preferably a transition metal, the Z's are the "tentacles" useful for bonding to a surface; and the Y's and X's form the rotor blades of the rotor portion. The Z's may be the same or different. A simple Z is —Hg—S—Z', where Z' is —$(CH_2)_n Si(OR)_3$ where n is an integer from 0 to 15, preferably from 0 to 5 and R is an alkyl group, preferably a short alkyl group with from 1 to 5 carbons. X may be an aromatic ring with p-substituents that are polar or charged. Y may be a similar aromatic ring with opposing p-substituents. Other substituents for X and Y are well known in the art.

Other larger structures are shown below.

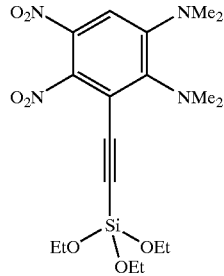

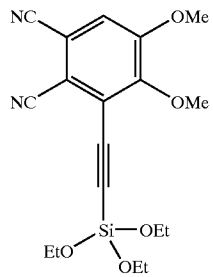

In the structures shown herein, the following combinations of substituents may be used, for example:(1) X=$NO_2$, Y=$NMe_2$, T=C; (2) X=$SO_3^-$; Y=$NMe_3^+$, T=C; and (3) X=$CH_3$, Y=O, T=N.

Another large dipolar rotor is shown below:

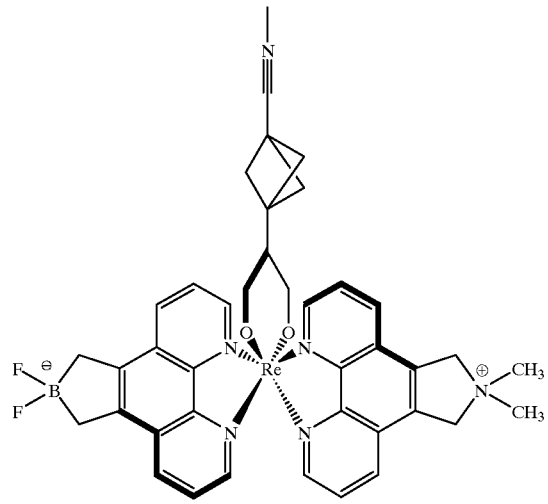

An example of replacing the base of structure 3 with a different base is shown below:

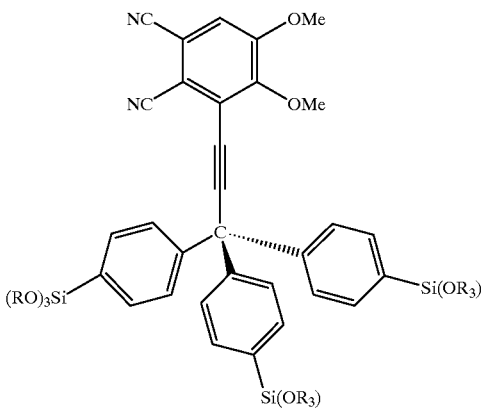

where R is an alkyl group.
Other large dipolar rotors are shown below:

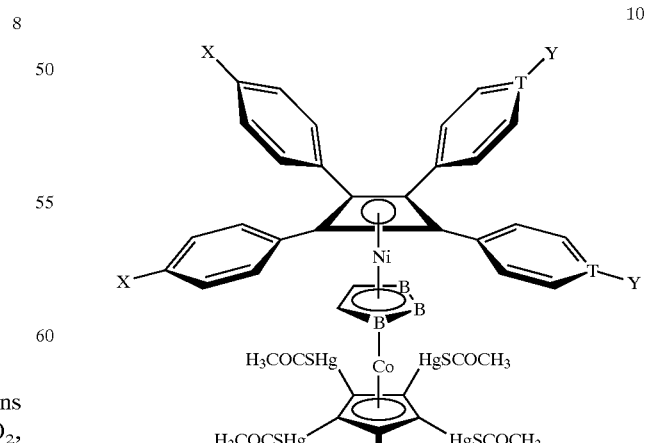

-continued

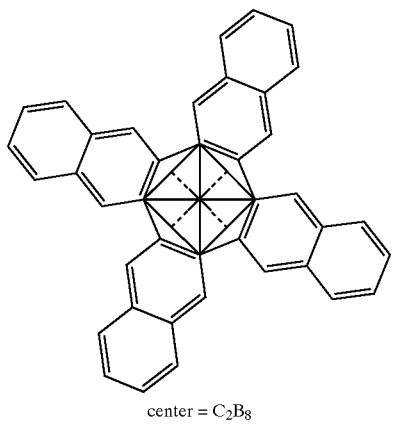

center = C₂B₈

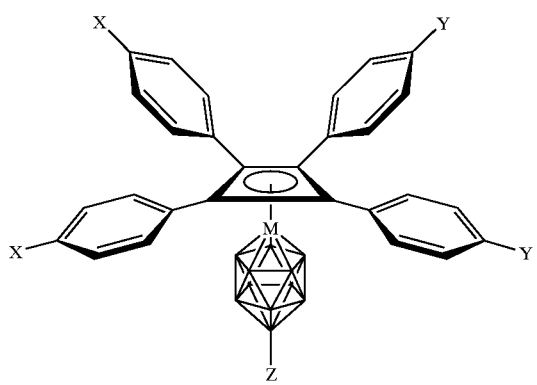

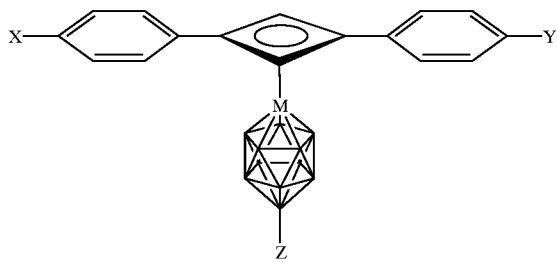

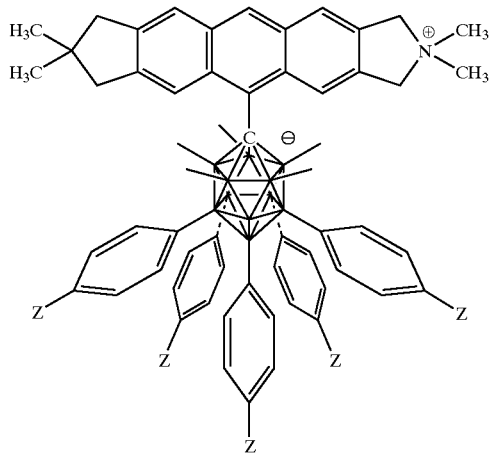

FIG. 1 shows an example of a specific surface mounted molecular dipolar rotor.

Both single dipolar rotors and 2-dimensional arrays of interacting dipolar rotors are described.

Organic synthesis of the molecular dipolar rotors can be used to engineer all important properties. Properties such as the size and moment of inertia of the rotor portion, its height above the surface, the rotational friction, the magnitude of the dipole and the spacing of an array of dipoles, and thus ultimately its Curie temperature (the temperature at which ferromagnetism changes to paramagnetism), propagation velocities, dissipation, etc., can be controlled by design of the chemical structure and choice of base, axle, rotor and bearing elements making up the dipolar rotor and of the location of the dipolar rotors in the array (geometry of the array and inter-rotor distances).

The rotors may be driven to cause the dipole to move or oscillate. The rotors may be driven in a variety of ways, such as pendulum-type motion of the axle and rotor, or rotational motion of the rotor portion. The latter is preferred in many applications, because it has no characteristic frequency. The rotors may be driven in a variety of ways, such as electrically, magnetically, mechanically or optically. Driving the rotor with an alternating electric field induces detectable current in nearby electrodes. Even a single two-dimensional layer of dipolar rotors contains sufficient polarization density to be useful in electronic devices.

Methods of synthesis of dipolar rotors are determined by one of ordinary skill in the art without undue experimentation. In addition to the synthesis and construction methods described herein, other synthesis and construction methods are described in U.S. Pat. No. 5,876,830 (issued Mar. 2, 1999 to Michl et al.), hereby incorporated by reference to the extent not inconsistent with the disclosure herein. Methods of using the dipolar rotors are described herein, or easily determined by one of ordinary skill in the art without undue experimentation.

DETAILED DESCRIPTION OF THE INVENTION

The following description is intended as a nonlimiting discussion of particular embodiments.

Figure 1:
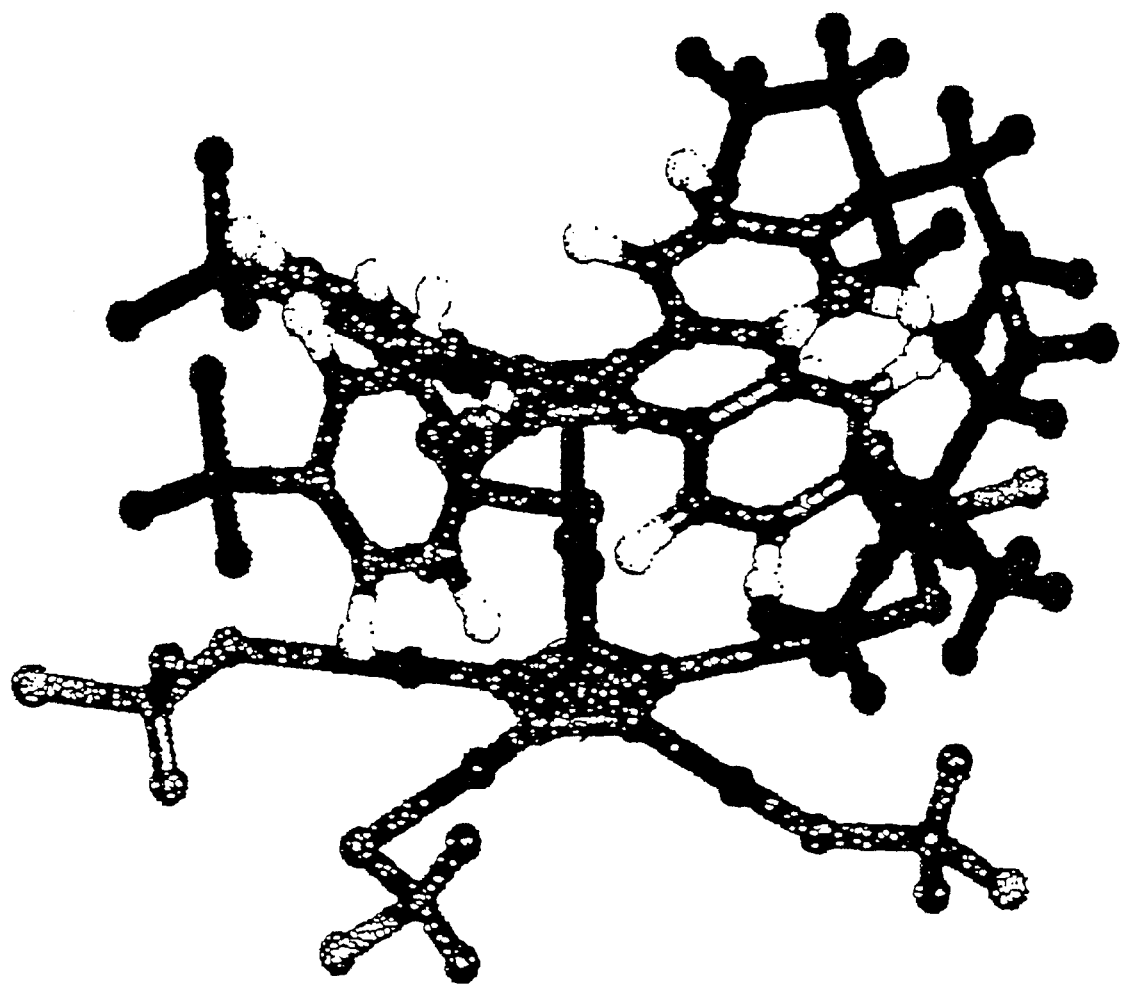
FIG. 1 is an example of a large dipolar rotor.
Figure 2:
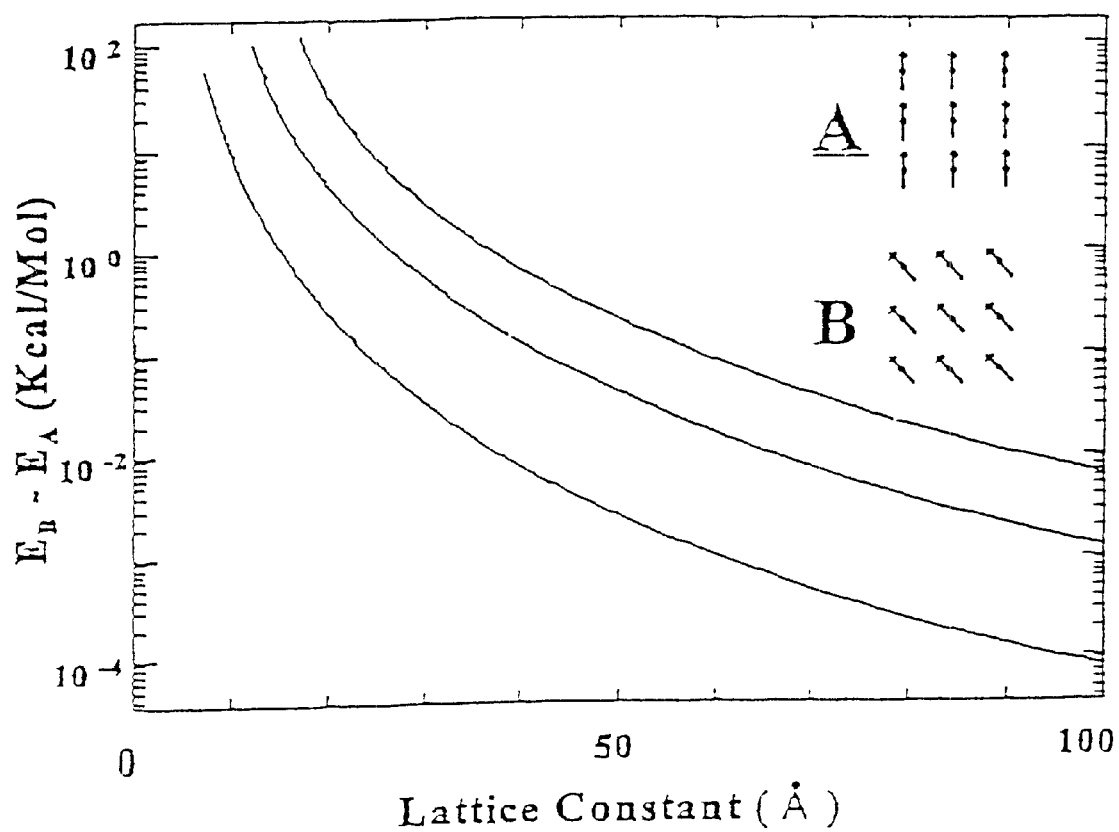
FIG. 2 shows the energy difference between two orientations of a square array of perfectly aligned dipoles of three magnitudes as a function of separation.

An array of SMDRs on a surface will be polarizable, with distinct dielectric properties, since an SMDR has no intrinsic spring constant or resonant frequency, and its response to an outside field is very nonlinear. Transient perpendicular polarization is induced as the SMDR is switched from one extreme orientation to the other. This is shown in FIG. 2, where the energy difference between two orientations (B) and (A) of a square array of perfectly aligned dipoles of three representative magnitudes (from the top: 72 D (rotor length 15 Å), 48 D (rotor length 10 Å) and 24 D (rotor length 5 Å)) is shown as a function of separation between the orientations (calculated for $10^6$ lattice points in a square array).

The rotors and rotor arrays have many applications as polar electronic materials (paraelectric, ferroelectric, piezoelectric, pyroelectric, etc.) and are useful in reducing the size of voltage-tunable filters, oscillators and phase shifters, as well as in sensors, actuators, delay lines and resonators. Other uses can be envisioned by those of ordinary skill in the art.

Two relatively simple applications are described as examples. Varactor diodes are discrete electronic components used primarily in analog RF and microwave circuits. They are nonlinear capacitors made from reverse-biased p-n junctions or Schottky barriers in either silicon or GaAs. Usually, a large control voltage is used to tune the effective small-signal capacitance. Most varactors are used as tuning elements in voltage controlled oscillators, but improved devices would have applications in voltage-tunable filters and phase shifters. Existing devices have large effective series resistances, especially at microwave frequencies where quality factors (Q values) of 20–50 are typical. These could be replaced by dielectric varactors containing 2-d dipolar rotor assemblies in the paraelectric phase. Strong dielectric nonlinearity would occur in this phase. In the usual inorganic dielectrics that have been considered for these applications the intrinsic loss mechanisms are due to coupling of the soft mode to other phonons. The rotary degrees of freedom can be strongly decoupled from phonon modes to reduce the dielectric dissipation. These structures are useful as tuneable oscillators, tuneable phase shifters, tuneable band pass filters, and tuneable notch filters.

Figure 3:
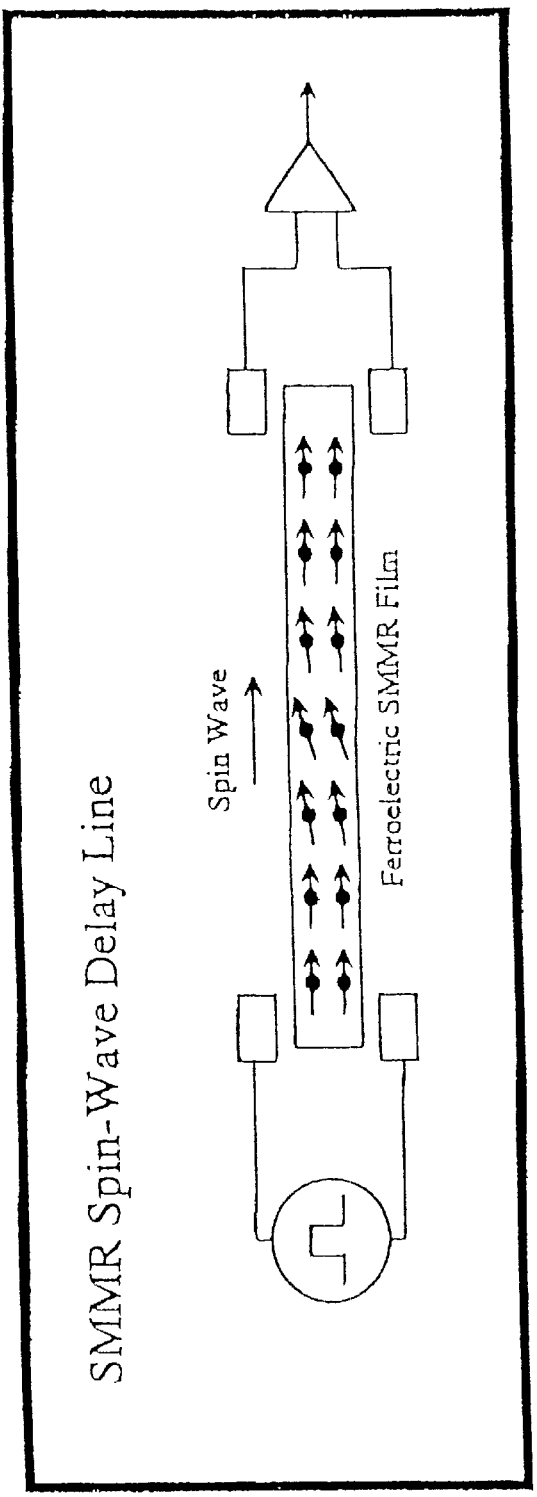
FIG. 3 shows a polarization-wave analog delay line.

A unique feature of the polar arrays is extremely low spin-wave propagation velocities. According to a 1-dimensional simulation, velocities of order 1 m/s are the norm. This occurs because the rotation of a single rotor is essentially unconstrained, the moment of inertia is very large, and the rotor-to-rotor interactions may be adjusted over a wide range. One application of this concept is a polarization-wave analog delay line such as that shown in FIG. 3. In this figure a strip with a ferroelectric array of ordered rotors is shown with two pairs of electrodes located in the vertical direction. A pulse is applied to one set of electroes which causes the dipoles to change orientation. When this pulse is released, the dipoles near the electrodes return to their original orientation. However, a pulse is propagated through the adjacent dipoles through the strip.

The pulse arrives at the corresponding set of electrodes with a delay that is determined by the rotor structures. In this manner, a small strip can be engineered to produce a desired delay. Low propagation velocities imply that devices operating at a given frequency can be made more compact. This is the same argument that leads to the use of surface acoustic wave devices. The ubiquitous quartz and perovskite ceramic resonators used in RF electronics have properties which are controlled by typical inorganic sound velocities of order 1000 m/s. The materials here allows the size of frequency control and filter devices to be dramatically reduced leading to on-chip solutions for frequency control and filtering functions.

Referring to structures 4 and 5 shown above as examples, in these structures, Z=may be any of a variety of structures that give the desired attachment to a surface and the desired level of stability. One particular Z is —$(CH_2)_n Si(OR)_3$, where n=1-12, R is hydrogen or alkyl group having from 1 to 6 carbon atoms. In the structures, X and Y may be a variety of substituents, as described above. Particular structures useful for X and Y include $N^+Me_3$ and $SO_3^-$; and $NO_3$ and $NMe_2$. The structures 4 and 5 have low (~1 kcal/mol) barrier to rotation about the axis of metal-π-face sandwiches, large accessible dipole (easily over 100 D), availability of substitution sites for mechanical balancing, a rotor portion size that prevents suitably chosen blades from touching the substrate, resistance to rotation axis tilt provided by the wide lower deck, mechanical inertia against tugging by an outside electric field provided by the massive Hg atoms, and allow ease of attaching five reactive "tentacles" that offer sturdy covalent mounting to the substrate, even if some remain unused. Their length and rigidity are easily optimized, since various thiols can be attached to the Hg atoms of the bottom deck. The —$Si(OR)_3$ group attaches well to the surface of $SiO_2$.

The dipole is largest (>100 D) when X and Y in 4 carry opposite charges. Since they are ~15 Å apart, there is a risk that they might attract random counterions, ruining the rotor action, or be attracted to the substrate excessively, thwarting the desired orientation in the mounting step. One possibility is to use 4 with dipolar groups X (pyridine N-oxide, mechanically balanced by Y $CH_3$, for example). This yields a dipole of ~6 D. Another is to use two positively (X) and two negatively (Y) charged groups in 4 and 5. The charges on the trialkylammonio (X=$RR'R''N^+$) and sulfonate (Y=$SO_3^-$) groups are highly concentrated. If this causes excessive attraction to the substrate, attachment can be done with X and Y neutral (RR'N and $SO_3R$), and the charges developed subsequently (alkylation, hydrolysis). The more diffuse charge on tropylium (X=$C_7H_6^+$) and carborane (Y=$CB_9H_9^-$ or $CB_{11}H_{11}^-$) may be used to avoid adhesion of random counterions. Other polar or charged groups may be used. The rotor must be balanced by choosing the substituents on the ammonio nitrogen, the tropylium ring and the carborane cage in the examples described above.

The rotor blades in 4 are centered only 3.4 Å above the bottom deck, their charge attracts them to the tentacles, and they frequently collide with the mercury atoms. In contrast, in 5, the rotor blades are well above the tentacles and the rotation is less constrained than that of 4. Tetra-decker molecules may be used, as well.

As known in the art, molecules are readily synthesized using methods known in the art or modifications of methods known in the art.

Surface Mounting.

Figure 4:
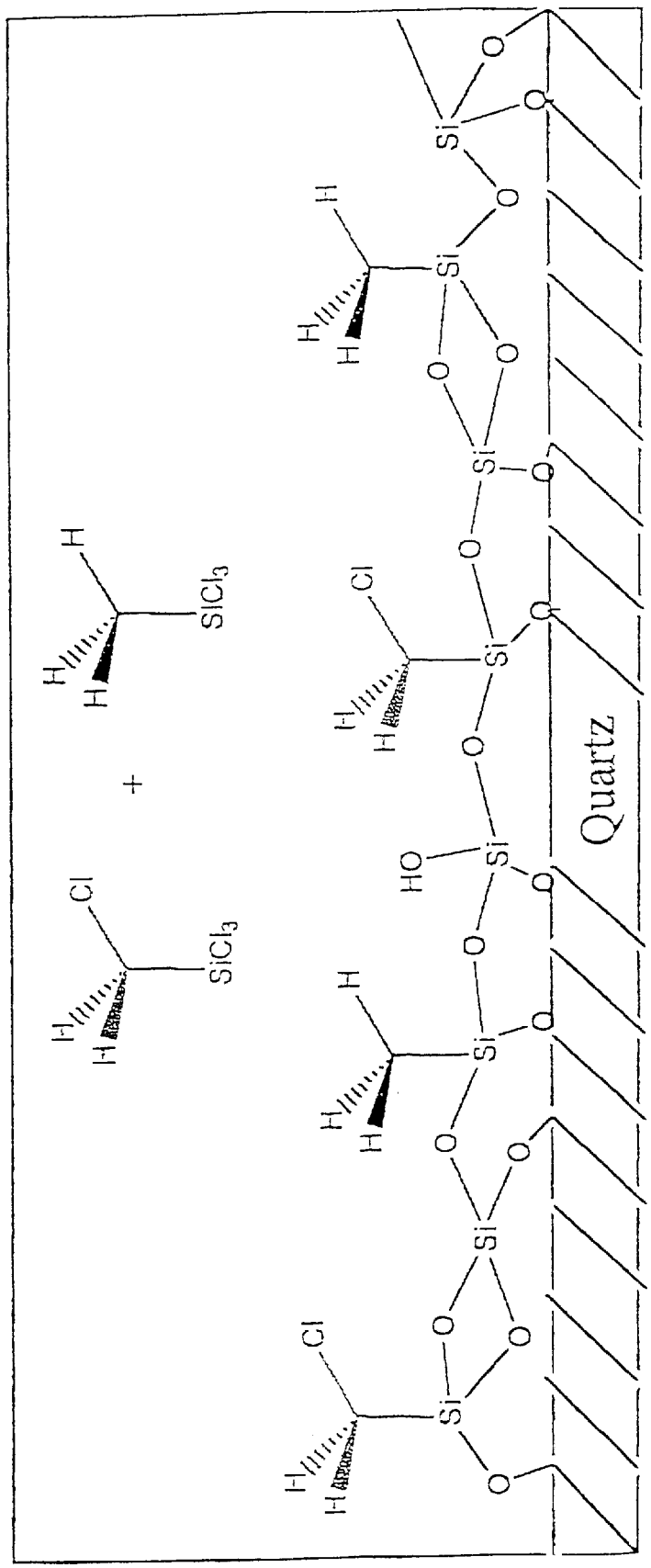
FIG. 4 shows an example of dipole rotors mounted on quartz.

The presence of five flexible tentacles provides good solubility. The molecules are attached to an $SiO_2$ or similar surface from dilute solution in a polar solvent and the deposited surface concentration is controlled by the choice of bulk concentration and treatment time. An example of surface mounting is shown in FIG. 4. Charged groups may adhere too strongly to the surface and prevent proper anchoring of the tentacled pedestal (particularly the small groups; less so those with more diffuse charges). If so, a neutral precursor is adsorbed and the charges are unmasked later (e.g., a sulfonate ester is deposited and hydrolyzed in situ, or a tertiary amine is quaternized in situ). The surface area for the deposition can be defined by lithography, and for single-molecule experiments can be quite small (an even smaller area can be defined with an STM tip).

Surface concentration is monitored by methods such as Auger spectroscopy, ESCA, grazing incidence and/or ATR FTIR, resonance Raman, and EELS, which also provide information on the orientation of the SMDRs.

Characterization of Arrays of SMDRs

The usual dielectric measurements can be performed despite the fact that a single molecular layer is under consideration. Moreover, the polarization density in these materials is large enough to allow useful electronic function from a single molecular layer.

Figure 5:
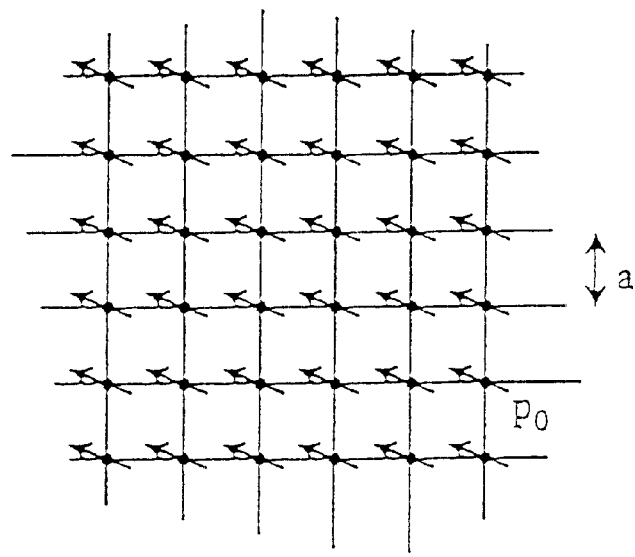
FIG. 5 shows a two-dimensional array of SMDRs.
Figure 6:
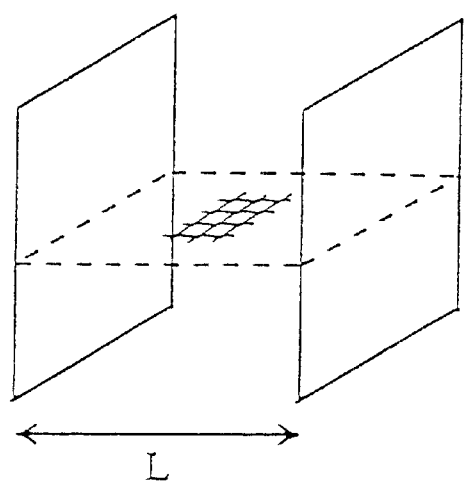
FIG. 6 shows a SMDR array placed between parallel plates with spacing L and area $L^2$.

A 2-d array of SMDRs shown in FIG. 5. A lattice constant $\alpha$ of 2 nm is considered and dipole moments $p_0$ of 50 D. The figures show regular square arrays, but the theory applies equally to random arrays of the same average density. Electronic measurements on polar dielectrics are made by placing the material between conducting plates and measuring the charge versus voltage relationship Q[V], which is normally hysteretic and nonlinear. Effects are detectable when the saturation charge (for paraelectrics) or spontaneous charge (for ferroelectrics) makes a measurable voltage across the capacitor. Consider first the parallel plate capacitor shown in FIG. 6, where the geometry is described by the single length scale L. Suppose that a single molecular layer of 2-d dipole array is placed in the capacitor. The areal spontaneous polarization density is $p_0/\alpha$, and this is also the effective linear charge density at the edge of the 2-d array due to the divergence of polarization. Thus the total charge induced on the plates is given by $Q=(p_0/\alpha)L$. This charge results in a remnant voltage of V=Q/C across the capacitor of $V=p_0/\epsilon_0\alpha$.

A remnant voltage of about 5 V will result, independent of the capacitor length scale. This is easily detectable. In the simplest practical case L≅1 mm. This leads to a very small capacitance of a few hundredths of a picofarad, which is much less than the input capacitance of any conventional preamplifier. However, with a typical input capacitance of 1 pF the resulting signal attenuation by a factor of 100 is still perfectly acceptable. It is therefore straightforward to perform Q[V] measurements on single molecular layers. Using readily available JFET preamps measurements are made from very low frequencies up to at least 10 MHz. JFET front-ends are easily incorporated into cryostats to allow measurements down to 4 K.

Measurements of this kind reveal the basic thermodynamic properties of the disclosed arrays. The Curie or glass transition temperature, and the remnant and saturation polarizations can all be measured.

Figure 7:
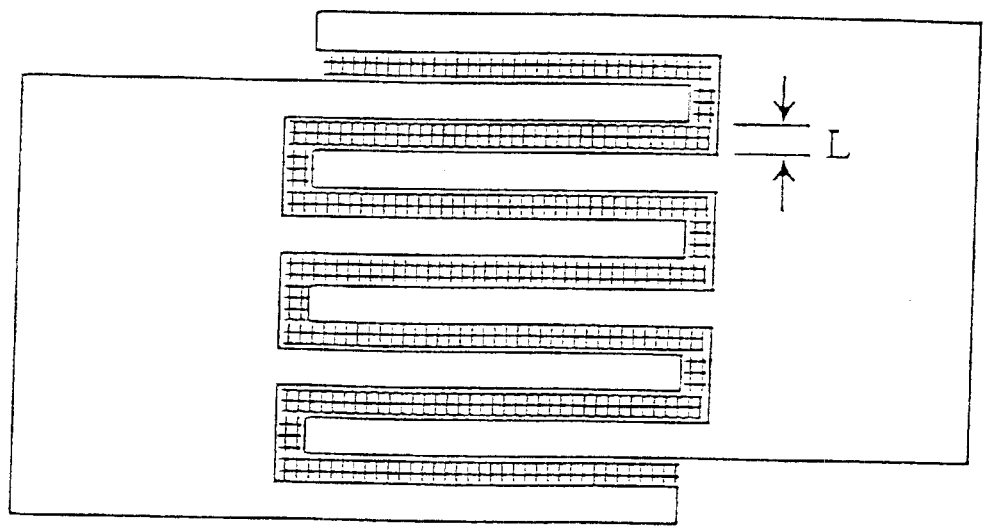
FIG. 7 shows an interdigital coplanar capacitor with gap L and meander length nL.

The very small capacitance of the structure just described is not ideal for electronic device applications. However, the coplanar meander electrode structure shown in FIG. 7 can provide practical values of capacitance with a single molecular layer. The capacitance of a length L of the meander is still approximately $\epsilon_0 L$ as for the parallel plate, but with meander length nL there are now n such capacitors in parallel. Ordinary optical lithography techniques can achieve at least n=1000 in a 1 mm$^2$ area, so that picofarad capacitances can be reached.

These values are comparable to line impedances at microwave frequencies, and therefore have applications to microwave dielectric varactors and phase shifters.

For measurements these materials are incorporated in coplanar meander capacitors of just the sort described here.

A method has been developed to accurately relate the observed capacitance to the material properties. In addition, microstrip resonator techniques have been developed to allow the temperature and field dependence of paraelectric dielectric films to be measured from 300 K to 4 K and from audio frequencies up to 20 GHz. These techniques will be applied to any materials found in the present study which show promise for microwave dielectric varactor application.

Single Rotor.

Experiments on single SMDRs address basic questions concerning molecular rotor mechanics.

Figure 8:
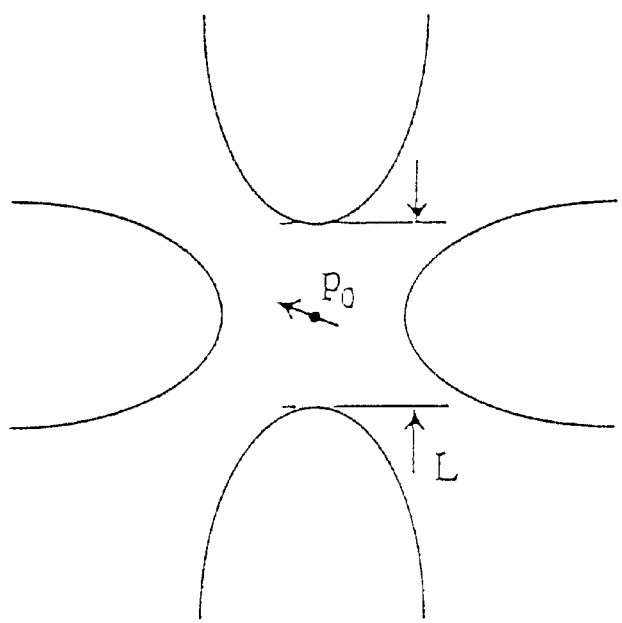
FIG. 8 shows a single SMDR with dipole moment p0 located between four planar electrodes with length scale L.

As an example, four planar electrodes surround one single SMDR, as shown in FIG. 8. As before, the electrodes are characterized by a single length scale L. The rotation of the dipole is equivalent to the motion of a charge q through a distance dx, with $p_0=qdx$. This motion induces an ac charge of amplitude $dQ=q(dx/L)$, or a current amplitude of $I0=\omega p0/L$, for rotation frequency $\omega$.

Figure 9:
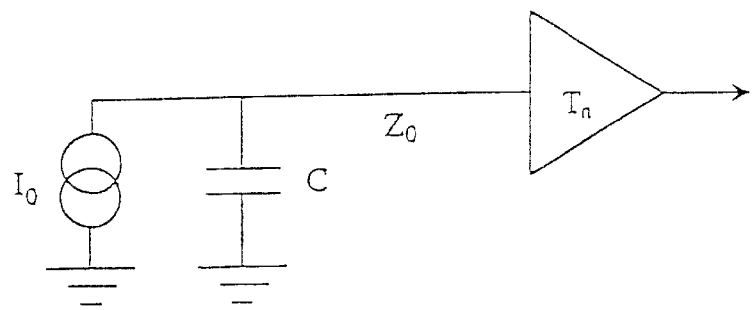
FIG. 9 shows the equivalent circuit for detection of a single rotor. The signal current $I_0$ is applied to low-noise amplifier with noise temperature $T_n$ via a transmission line with impedance $Z_0$. There is also a shunting capacitance C.

Suppose now that opposing electrodes are connected to a low-noise preamplifier via a transmission line. An equivalent circuit is shown in FIG. 9. The shunting capacitance C is due to the electrode—electrode capacitance and any additional stray capacitance necessary to connect the electrode structure to the transmission line. The signal-to-noise ratio is then given by the signal power $I_0^2 Z_0$ divided by the measurement bandwidth B times the noise energy, $S/N = I_0^2 Z_0/BkT_n$, where $T_n$ is the noise temperature and k is Boltzmann's constant.

The signal-to-noise ratio is thus proportional to the square of the ratio dx/L, and to the square of the signal frequency. It is therefore important to use the smallest possible electrode length scale and to work at high frequencies. Electrodes are fabricated from thin metal films using electron beam lithography and frequencies in the neighborhood of 10 GHz are used. Using the parameters L=100 nm, $\omega/2\pi$=10 GHz, $p_0$=50 D, $Z_0$=50 Ω, $T_n$=1—K, and B=1 Hz, a large signal-to-noise ratio of 360 is found.

One possibility to drive the signal rotor is to use two opposing electrodes to provide a fixed frequency drive signal, and to use the other pair of electrodes to detect the motion. Simulation suggests that at 10 GHz the rotor will be underdamped even at room temperature, and therefore the rotor will follow the instantaneous electric field; in other words the dipole is parallel to the drive field at the instant of peak field. In this case the detected rotor signal is in phase quadrature with the drive signal. There is also an in-phase signal due to imperfect orthogonality between the electrode pairs, but this can be nulled with a trim capacitor between adjacent electrodes. The small measurement bandwidth required is obtained by synchronous detection using the drive signal as a reference. A low-noise cryogenic homodyne reflectometer have been developed for mesoscopic quantum transport measurements that uses a similar technique. The most important quality that is measured in this experiment is the rotational damping constant and its frequency and temperature dependence, since this determines the phase lag between the rotor and the drive frequency. Even if the damping is small so that the phase lag at constant drive frequency is immeasurably small, it can still be discerned by studying the response to frequency modulation of the drive signal.

This single rotor couples both with the external electromagnetic field permitting spectroscopic or scattering study) and with the environment, such as the $SiO_2$ substrate. This produces friction observable as damping of the rotor.

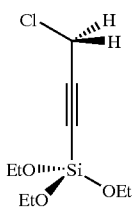

The deposition of rotors onto surfaces has been examined with the readily accessible analog of the rotor 15, diluted with the methyl form (i.e., the chlorine is replaced with a hydrogen), both without the triple bond. The material is deposited as a vapor at $10^{-6}$ torr in a vacuum chamber containing quartz with lithographically patterned electrodes, bare quartz and bare silicon. The latter substrate is used to determine layer thickness by single-wavelength ellipsometry and the composition of the deposited monolayer by Auger spectroscopy.

Dielectric Relaxation Measurements on Rotor Arrays

The goal of these measurements was to study the low frequency dynamics of both interacting and non-interacting rotor arrays. For non-interacting (low density) arrays, the equilibrium polarization and the relaxation time were measured. The equilibrium polarization depends on the product of the rotor density and the dipole moment per rotor, while the relaxation time depends on the barrier height for rotation and the attempt frequency. The arrays studied are disordered. At high densities (where interactions are important) the effects of this disorder is seen in both the equilibrium polarization and the relaxation response.

Measurement Technique

For electronic measurements rotor molecules analogous to the structure shown above (without the triple bond) were incorporated into a planar capacitor with gold interdigital electrodes, patterned on a quartz glass substrate using optical lithography. The gap between the electrodes was 10 $\mu$m wide and total capacitance was about 1.2 pF. The molecular rotors were deposited from a vapor onto the glass in the spaces between the gold electrodes.

Several features of the dielectric response can be used to distinguish the signal from the rotors from that due to the substrate. For rotors which are thermally activated, at low temperatures the polarization relaxation of the rotors is much slower than the substrate. This longer time-scale is used to separate the rotor signal from that of the substrate.

Figure 10:
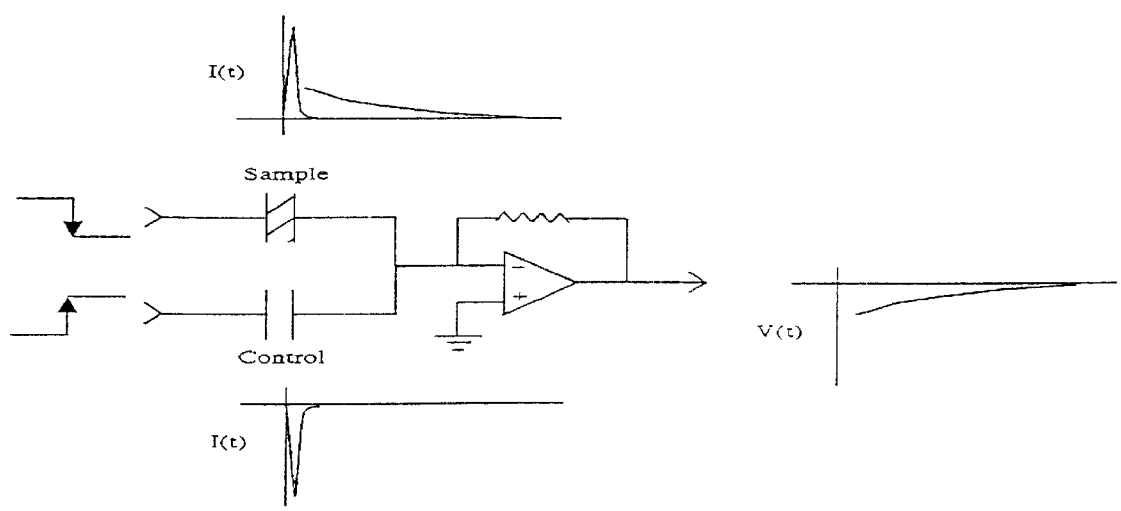
FIG. 10 shows a schematic diagram of the dielectric relaxation measurement apparatus. The output signal V(t) is proportional to the time derivative of the rotor polarization.

A schematic of the measurement apparatus is shown in FIG. 10. A 15 V potential difference is applied across the sample capacitor for a period long enough to establish equilibrium, and then the sign of the potential is changed in less than 1 $\mu$s. The resulting current through the sample capacitor is shown in the upper graph. There is a prompt response due to dielectric relaxation of the substrate and then a much slower relaxation as the rotors reorient. The prompt signal is nulled at the amplifier input by combining it with a similar response from a control capacitor. The control capacitor is kept in a liquid nitrogen bath so that its properties do not change with time. The resulting voltage signal at the output of the virtual ground amplifier is proportional to the time derivative of the mean rotor polarization, and thus its integral is proportional to the equilibrium polarization in the applied field.

In practice, the time-domain signal contains a residual signal at short times (<10 $\mu$s) due to imperfect balance between the two prompt signals, and a slower background signal which appears to be due to contaminant molecules on the substrate surface. The background relaxes in about 50 $\mu$s. Many time-domain sweeps are averaged on a digital oscilloscope to reduce the electronic noise. The resolution at present is about 1 fC for the total integrated charge flowing out of the) sample capacitor after the voltage step is removed. The resolution is highest for relaxation times in the 50–300 $\mu$s range.

The sample is located on the cold stage of a single-shot $^3$He evaporation cryostat and its temperature can be controlled from 400 K to 0.3 K. Rotors analagous to that shown above are frozen out below about 30 K.

For a non-interacting rotor array the integrated charge is given by $$Q = Nd\mu L(\mu E/2kT)$$

where N is the number of squares in the interdigital electrodes, d is the rotor area density, $\mu$ is the bare rotor dipole moment, and L is the interdigital electrode gap. The effect of thermal fluctuations is to reduce the charge by the Curie factor E/2kT, relative to the value for perfectly oriented rotors.

Figure 11:
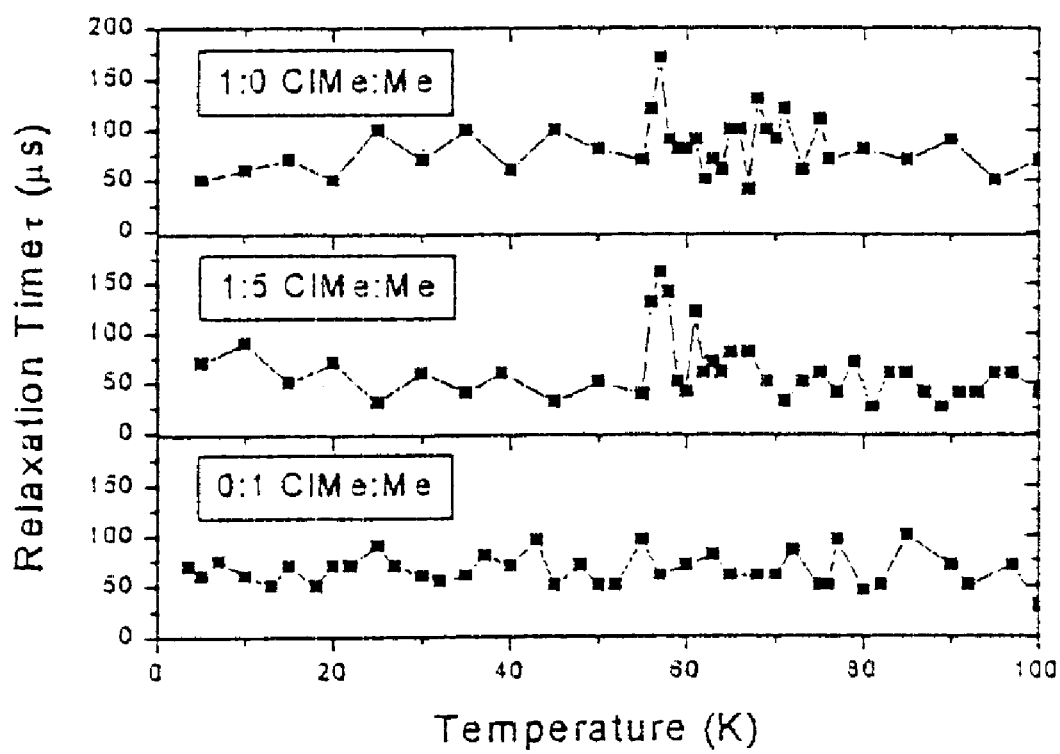
FIG. 11 shows polarization relaxation rate for rotors as a function of temperature.

In FIG. 11 results for the relaxation times for three samples, one with a $5 \cdot 10^{18}$ m$^{-2}$ coverage of rotors analogous to 1A (no triple bond) (upper graph), one with a coverage of $1 \cdot 10^{18}$ m$^{-2}$ (obtained by dilution with non-polar methyl rotors) (middle graph) and a control sample with only the latter rotors is shown (lower graph). The data displayed was obtained by fitting the time domain decay to two exponentials. The time constant of the slower decay is plotted. At most temperatures this is due to the background relaxation of about 50 $\mu$s, but over a narrow temperature range near 60 K the two samples with polar rotors show a much slower decay.

This narrow relaxation peak is what should be expected for non-interacting rotors with a large barrier height for rotation. The rotation is thermally activated and the relaxation rate varies rapidly with temperature, so there is a very narrow temperature range where the relaxation can be seen. If it is too fast it is lost in the electronic and background responses, and if it is too slow there is not have sufficient signal-to-noise ratio to see it. The central temperature and width of the peak correspond to an Arrhenius law with a barrier height of 1200 K and an attempt frequency of $10^{13}$ s$^{-1}$, which agrees nicely with expectations for these molecules based on a Hartree-Fock calculation on a simple model structure. The observed integrated current (proportional to equilibrium polarization) for the dilute (1:5) sample is one-third of the value expected from the rotor density, suggesting that either not all the rotors are active or the coverage estimates are in error. The observed equilibrium polarization for the full coverage sample is about 15 times smaller than expected for non-interacting rotors at that coverage. However, in this case the density is high enough that interactions are certainly important, and it may be that a large fraction of the rotors are frozen by rotor—rotor interactions. One might have expected that the full coverage sample would show slower relaxation or a broad range of decay times, but this is not observed. It may be that the observed signal reflects an inhomogeneous coverage, and comes mainly from regions of low density. Various amounts of diluent were studied (data not shown).

Figure 12:
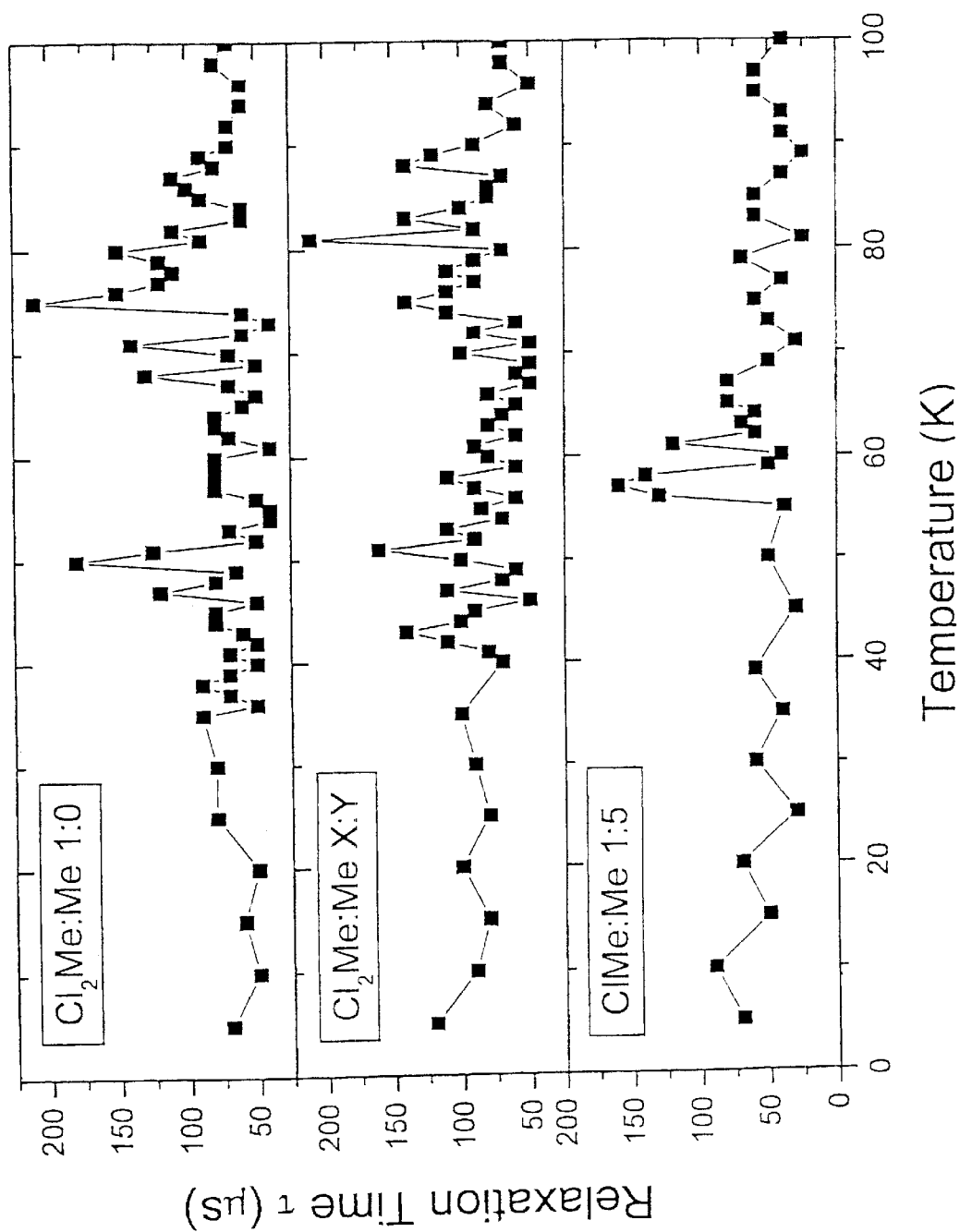
FIG. 12 shows polarization relaxation rate for rotors as a function of temperature.

FIG. 12 shows data for the dichloro analogue of the structure above. Data is shown for dichloromethyl without diluent (upper graph), for dichloromethyl with methyl diluent at some undetermined ratio (middle graph) and with five parts diluent to one part structure 2 above (lower graph).

Rotor Simulation—Individual Rotors

A classical molecular dynamics simulation using Newton's and Coulomb's laws, and the UFF force field taken from the literature, were used to simulate the response of the rotor 9 with a large dipole moment ($\mu$=42 debye) and moment of inertia ($1.5 \times 10^4$ $\mu$Å$^2$, where $\mu$ is the atomic mass unit), mounted in vacuum on a sizeable segment of a square grid polymer, to a rotating electric field. The time steps used for integration were 2.1 fs. A total of 171 dynamics runs at electric fields ranging from 100 to 7000 kV/cm in strength and from 3 to 200 GHz in frequency lasted over 100 ns. The starting temperature was 150 K, such that kT was barely above the calculated rotational barrier of ~0.3 kcal/mol, and it changed very little during a run. To evaluate the performance of the rotor, seven quantities were monitored continuously during each run, such as the rotor angular momentum and the accumulated angular lag a of the rotor behind the field ($\alpha$ is normalized in a way that makes $\alpha=0$ correspond to no field turns skipped, or perfect response, and $\alpha=1$ to all field turns skipped, or no response). In the absence of a driving field, the rotation of the rotor decayed in time approximately exponentially, with a relaxation time of ~80 ps.

For fields that are sufficiently strong and frequencies that are sufficiently low, the rotor acts like a synchronous motor and turns with the field. At each frequency, a minimum "break-off" strength of the electric field is required ($E_{bo}$), below which the rotor fails to rotate at all ($\alpha=1$). Taking the value $\alpha=1/e$ as the maximum permissible if a rotation is to be considered perfect, the critical field strength $E_c$ is defined to be the weakest field required to assure this condition. Classical friction and random thermal motion were identified as the two factors that oppose smooth rotation of the molecular motor. In order to provide a phenomenological characterization of the rotor in terms useful for statistical treatments of large rotor arrays, a simple model was used, based on the Arrhenius equation and containing only one adjustable parameter, namely a friction constant, allowed to be a function of frequency. This permitted an excellent fit of all the a values obtained in the simulations (within their statistical uncertainties due to limited run lengths), and produced the predictions for $E_{bo}$ and $E_c$.

Rotor Simulation—Rotor Arrays

The effective transport of energy and signals in adlayer assemblies constitutes the functional heart of an entirely new approach to molecular signaling and response. After an initial study of simple longitudinal dipole chains, work on ordering, excitations and signal transport in transverse molecular dipole chains has now been published (Sim, E., Ratner, M. A. and deLeeuw, S. W. *J. Phys. Chem. B*, 103, 8663–8670). The dispersion relation for these transverse dipoles is far more similar to that for phonons than was the case in our earlier work on longitudinal dipole chains. These also support soliton-like excitations down the chain, excitations that can result in signal transport, signal processing, and addressability of remote sites at intersecting lines.

The dielectric response of arrays of dipolar rotors is intrinsically non-linear and therefore theoretically and even practically interesting. Analyses of a particularly simple situation, a one-dimensional string of rotors interacting by electrostatic forces, suggest that solitary waves may be possible. The statistical physics of interacting rotors in two dimensions is likely to be of special importance, considering the strong current interest in 2-D spin glasses.

Figure 13:
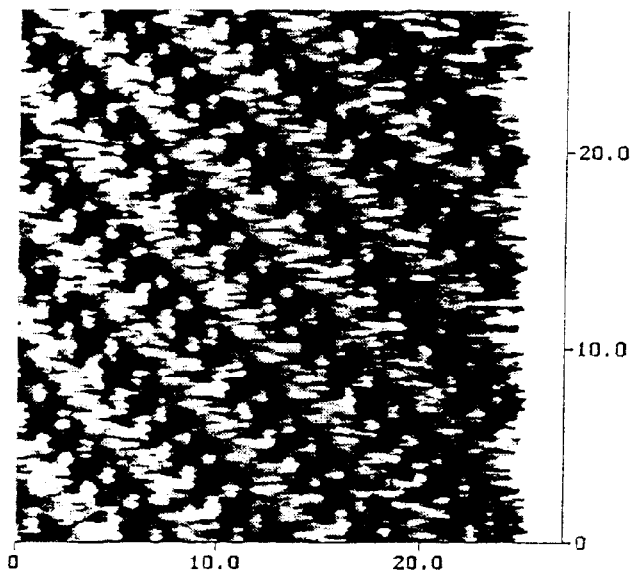
FIG. 13 shows an STM image of a self-assembled regular grid on graphite surface.

The basic device is a surface-mounted mechanically balanced molecular dipolar rotor, exemplified as 9 above. The axle is ready for attachment to a grid point in a square grid array; the bearing consists of a single covalent bond, a fundamental element of molecular-scale mechanics. FIG. 13 shows an STM image of an example of a surface-deposited regular structure that is used as anchor to fabricate arrays of rotors.

The response of a firmly anchored molecular dipolar rotor to an outside rotating electric field represents one of its fundamental characteristics and it is useful to consider it in some detail in order to gain insight into a general issue that distinguishes molecular from macroscopic machinery, namely the non-negligible role of random thermal motion. Qualitatively, one would expect the rotor to follow the circular motion of the field if the latter is sufficiently strong and its frequency is not excessive, provided that the strength of the field-rotor interaction exceeds the effects of random thermal fluctuations, and provided that the barrier to rotation is not prohibitive. The extensive computer simulations that have been performed for the rotor 9, with a dipole moment of $\mu=42$ debye and moment of inertia of $1.5\times10^4$ amu.$\Omega^2$, attached to a square polymer grid, allow expression of these expectations in a more quantitative fashion. Although the simulations were all run at a single temperature (150 K), and for only one very low value of the rotational barrier (~0.3 kcal/mol), extrapolations are possible. The general principles outlined below remain valid for other cases of low rotational barrier.

In general, the dipolar rotor lags behind the driving electric field, and after n turns of the field the cumulative lag angle is $\alpha$. The mean lag per turn, $a=\alpha/2\pi n$, is used to evaluate the performance of the rotor. At a constant field frequency $\omega=2\pi\nu$, the lag is close to 0 and the rotor follows the field perfectly if the field amplitude E is very large, acting as a synchronous motor. As E is reduced, the lag a increases and at a critical value $E_c$, it reaches the value $1/e$. Now, the rotor skips a fair fraction of turns of the field and acts as an asynchronous motor. As E is reduced further, a rises rapidly, and at the break-off field $E_{bo}$ it becomes indistinguishable from unity, at which point the rotor does not function as a motor at all. The dependence of $\log E_c$ and $\log E_{bo}$ on $\log \nu$ is shown by the bars in FIG. 14, (bar lengths indicate statistical uncertainties due to finite length of the simulation runs). At frequencies below ~40 GHz, $E_c$ and $E_{bo}$ are independent of $\nu$, as the important factor that limits rotor performance is random thermal motion. Indeed, $E_{bo}$ rapidly converges to the value $kT/\mu$, at which the dipole-field interaction $E\mu$ equals kT, while $E_c$ converges to a similar limit, but much more slowly. At frequencies above ~40 GHz, $E_c$ and $E_{bo}$ grow approximately with the second power of $\nu$, as would be expected for a classical rotor whose "friction constant" $\eta$ is proportional to frequency. In this region, $E_c$ and $E_{bo}$ are high enough that the thermal energy kT is negligible relative to $E\mu$, and the rotor behaves as a macroscopic body.

Figure 14:
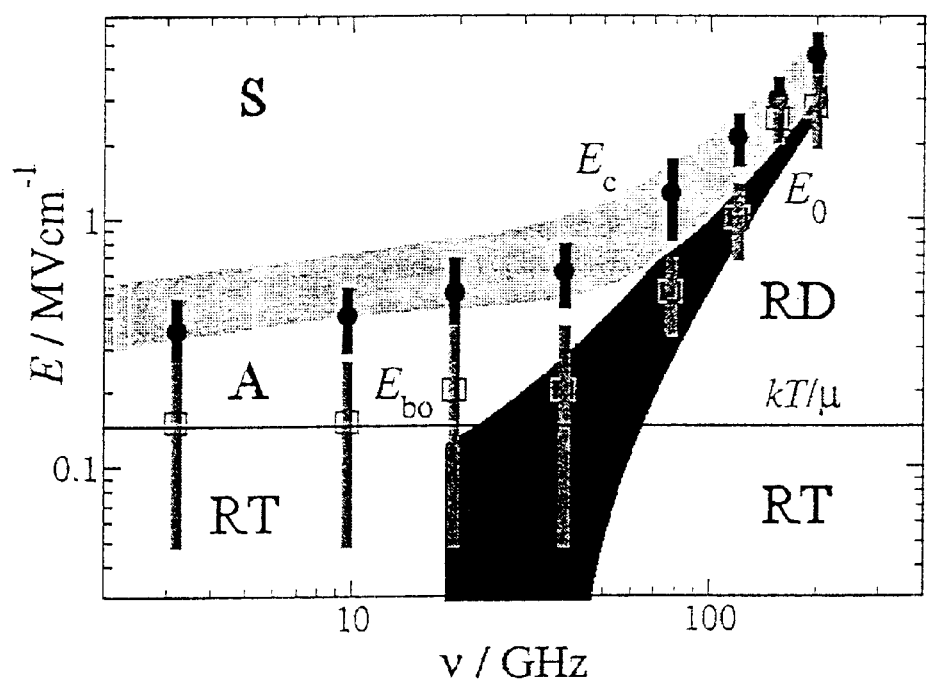
FIG. 14 shows critical (Ec) and break-off (Ebo) field strength from simulations (dark and light points, respectively) and critical (Ec) and zero-temperatures limit break-off (Eo) field strength from a model (light and dark band, respectively). Four regions of rotation regimes are labeled: S, synchronous; A, asynchronous; RD, random driven; RT, random thermal.
Figure 15:
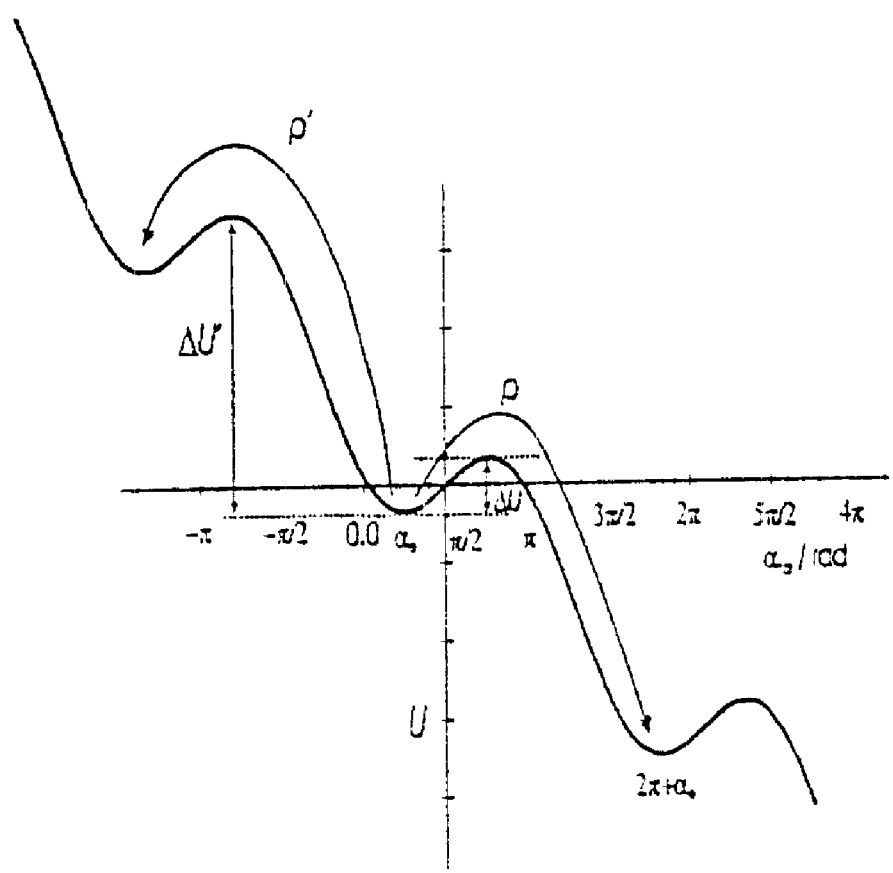
FIG. 15 shows the potential energy of an electric field driven rotor in a rotating coordinate syst.

It is possible to fit the $E_c$ points (bars) shown in FIG. 14 using a simple "tilted washboard" model in which thermal motion at 150 K is allowed to act on a rotor moving in a sloping potential imposed by friction (responsible for a drag torque $\eta\omega$, with $\eta$ assumed proportional to $\nu$), onto which a cosine function of the total lag angle $\alpha$ due to the electric field has been superimposed, in a system of coordinates rotating with the field (FIG. 15). The only adjustable parameter to fit is the proportionality constant between $\eta$ and $\nu$, which is found to be 1.14 eVps/THz for this particular rotor; the light band in FIG. 14 indicates the fit for $E_c$ (the width of the band indicates the uncertainty). The result for $E_{bo}$ that would be expected at 0 K ($E_0$) is shown as a dark band and the agreement with the high-frequency limit of the results obtained at 150 K is obvious.

Numerically integrated Langevin or Brownian dynamics including a stochastic force provide a more complicated but also more accurate model the motion of the rotor. Interestingly, the Brownian equations of motion for the molecular rotor are identical with the equations describing the i-v characteristics of a Josephson junction (JJ) with the variable i defined as $i=\omega/\omega_0$, where i is the JJ current. The Josephson junction voltage v relative to the current can be expressed as $v/i=<d\alpha/dt>/\Omega\sim\alpha/t\omega$, where t is the total time. For our rotor the usual McCumber parameter $\beta_C$ and thermal parameter $\Gamma$ are $\beta_C=E\mu I/\eta^2$ and $\Gamma=2\pi kT/(E\mu)$. Although many numerical results for Josephson junction plots have been published, few results are available for the parameters values relevant for our rotor, $\beta_C \cong 4$ and $\Gamma \cong \sim 1$. We note that for $\beta_C \cong 4$, the results predict that the motion of our rotor will be hysteretic: once regular rotation is induced by an above-critical electric field, the field will have to be reduced to about 70% of the critical value before the rotor stops moving synchronously.

Synchronous, Asynchronous, Random Driven, Random Thermal and Hindered Regimes of Rotation.

Based on FIG. 14, five regimes of molecular rotor behavior are dictated by the relative importance of random thermal forces described by kT, of the strength ($\mu$E) of maximum interaction of the dipolar rotor with the rotating electrical field, of the friction constant $\eta$ that describes the break-off drag torque, and of the rotational barrier height W.

(i) Synchronous Rotor Regime.

When $\mu E > \mu E_c$,kT,W, the rotor follows the rotating field slavishly and rotates at its frequency $\nu$. Points located above the $E_c$ line in FIG. 14 correspond to synchronous motion.

(ii) Asynchronous Rotor Regime.

When $\mu E_c > \mu E > \mu E_{bo}$,kT,W, the rotor turns in the direction of the rotating field but at a frequency lower than $\nu$ since it breaks off and skips a turn every now and then. Points in FIG. 14 located between the $E_c$ and $E_{bo}$ curves correspond to asynchronous motion.

(iii) Random Driven Rotor Regime.

When $\mu E_c,\mu E_{bo} > \mu E > $kT,W, friction is excessive. The rotor cannot keep up with the rotating field and performs irregular motion. Points in FIG. 14 located below the $E_{bo}$ curve and above the kT/$\mu$ line correspond to random driven motion.

(iv) Random Thermal Rotor Regime.

When kT>$\mu$E,W, the rotor exhibits nearly random thermal fluctuations with a slight preference for rotation in the sense of the rotating field. Points in FIG. 14 located below the kT/$\mu$ line correspond to random thermal motion (at T=150 K, $\mu$E equals kT at E=1.4 kVcm$^{-1}$). The independence of $E_c$ and $E_{bo}$ of $\nu$ in the limit of low frequencies is unlike anything observed for macroscopic rotors at ordinary temperatures (v) Hindered Rotor Regime.

This regime is not illustrated in FIG. 14, which was obtained for a case in which the rotational barrier W was comparable with kT. When W>kT,$\mu$E, the rotor will be trapped in one of the minima on the potential energy surface, only infrequently jumping from one orientation to another. To obtain correct results in FIG. 14 for fields E weaker than 150 kVcm$^{-1}$, the effect of the barrier, and possibly also quantization effects, will have to be included in the modeling. So far, our simulations have all been performed at higher field strength or at kT$\geq$W.

Vertical shaft rotors consist of two segments that can rotate against each other easily, since they are joined with one single bond (barrier W, ~3 kcal/mol) or a linear single-triple-single bond combination (W<~0.2 kcal/mol), or with a single metal atom sandwiched between planar rings (W<~0.2 kcal/mol). One of the segments is functionalized in a way that permits a firm covalent attachment to a surface or a grid point, the other is the rotor proper (it can carry a large dipole, it can be propeller-shaped, etc.).

The chemical functionalization needed for the mounting of the rotors is dictated by the nature of the substrate. For single rotors or random arrays of rotors on surfaces such as quartz or sapphire, silane chemistry is used. For mounting on gold, thiol chemistry is available.

Molecular Electronics

The application of molecules in electronics has become an important and exciting activity in industrial, DOD and academic laboratories. So far much of the work has focused on molecular optoelectronics, both for logic and for communications. Much of the rest has been devoted to charge transport in molecular systems (molecular wires, molecular junctions, molecular switches). There is, however, another application towards molecular electronics in which the rotors seem strikingly appropriate—this is the application to cellular automata devices. The rotational position of a rotor is a way to store information on molecular scales that will be more robust and persistent than storage in purely electronic degrees of freedom. Indeed, data storage in polar molecular conformation is used presently at larger scale in the technology of non-volatile ferroelectric memories. The rotational position of a dipolar rotor can be set by electric fields from charges transported in molecular wires. The rotor polarization can then serve as the gate charge of a molecular scale FET for readout of the rotational position. At molecular scales it seems likely that tunneling rates will always be too large to allow for persistent data storage in mobile FET gate charge. By attaching the charge to an very stable insulating rotor molecule it may be possible to bring the controlling gate charge much closer to the FET channel than would be feasible for charge delivered by transport through molecular wires.

The following references are hereby incorporated in their entirety to the extent not inconsistent with the disclosure herewith.

DeLeeuw, S. W.; Solvaeson, D.; Ratner, M. A.; Michl, J. "Molecular Dipole Chains: Excitations and Dissipation" J. Phys. Chem. B., 1998 (102), 3876.

Vacek, J.; Michl, J. "A Molecular 'Tinkertoy' Construction Kit: Computer Simulation of Molecular Propellers" New J. Chem. 1997 (21) 1259–1268.

Vacek, J.; Michl, J. "Molecular Dynamics Simulation of a Grid-mounted Molecular Dipolar Rotor in a Rotating Electric Field" Proc. Natl. Acad. Sci. 2001, in press.

Although the description above contains many specificities, these should not be construed to limit the scope of the invention, but as rather illustrating some of the presently preferred embodiments. Thus, the scope of the invention should be determined by the appended claims and their legal equivalents. All references cited herein are hereby incorporated by reference to the extent not inconsistent with the disclosure herein.

We claim:

1. A molecular dipolar rotor comprising:

a base;

an axle connected to said base and oriented substantially perpendicular to said base;

a rotor portion connected to said axle and having an electric dipole moment.

2. The dipolar rotor of claim 1, wherein the electric dipole moment of the rotor portion is substantially in the plane perpendicular to the axle.

3. The dipolar rotor of claim 2, wherein the electric dipole moment of the portion is greater than 2 debye.

4. The dipolar rotor of claim 1, further comprising:

a bearing connecting the axle and the rotor portion.

5. The dipolar rotor of claim 4, wherein said bearing is a metal-to-$\pi$-face bond.

6. The dipolar rotor of claim 1, wherein said base is covalently attached to a surface.

7. The dipolar rotor of claim 1, wherein said base is a carbon atom.

8. The dipolar rotor of claim 1, wherein said base is a silicon atom.

9. The diolar rotor of claim 1, wherein said axle is a single bond.

10. The dipolar rotor of claim 1, wherein said axle is a triple bond.

11. The dipolar rotor of claim 1, wherein said axle is a transition metal atom.

12. The dipolar rotor of claim 1, wherein said rotor is an a substituted aromatic ring.

13. The dipolar rotor of claim 6, wherein said surface is dielectric.

14. The dipolar rotor of claim 1, wherein said rotor portion comprises two or more substituents with opposite charges, wherein said substituents with opposite charges give the molecule a large dipole.

15. The dipolar rotor of claim 14, wherein said rotor portion has the following structure:

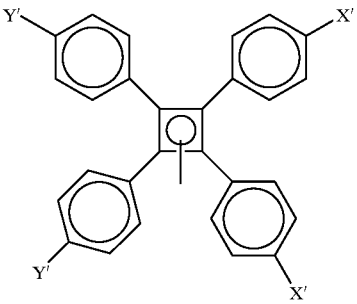

where X' is a positively charged substituent and Y' is a negatively charged substituent.

16. A surface-mounted array of dipolar rotors comprising:
dipolar rotors of claim 1 wherein the base is covalently attached to a surface.

17. The array of claim 16, wherein said surface is dielectric.

18. A device comprising:
a dipolar rotor of claim 1; and
an excitation source that can induce movement of the rotor portion of the dipolar rotor.

19. The device of claim 18, wherein said excitation source is one or more selected from the group consisting of: electrical forces, mechanical forces, magnetic forces or optical forces.

20. The device of claim 19, wherein said rotor portion of said dipolar rotates upon excitation by an alternating electric field, producing electric current by the alternating motion of the electric dipole of the rotor portion of said dipolar rotor.

* * * * *